(12) United States Patent
Kim et al.

(10) Patent No.: US 8,870,795 B2
(45) Date of Patent: Oct. 28, 2014

(54) METHOD AND APPARATUS FOR ANALYZING GAIT PATTERN

(75) Inventors: Min Ho Kim, Daejeon (KR); Ho Youl Jung, Daejeon (KR); Soo Jun Park, Seoul (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 522 days.

(21) Appl. No.: 13/295,735

(22) Filed: Nov. 14, 2011

(65) Prior Publication Data

US 2012/0166091 A1 Jun. 28, 2012

(30) Foreign Application Priority Data

Dec. 22, 2010 (KR) .................. 10-2010-0132340

(51) Int. Cl.
- *A61B 5/103* (2006.01)
- *A61B 5/117* (2006.01)
- *A61B 5/00* (2006.01)
- *G06F 19/00* (2011.01)

(52) U.S. Cl.
CPC ............ *A61B 5/1038* (2013.01); *A61B 5/6807* (2013.01); *A61B 2562/0247* (2013.01); *A61B 2562/046* (2013.01); *G06F 19/345* (2013.01)
USPC .......................................... 600/592; 600/587

(58) Field of Classification Search
CPC .... A61B 5/103; A61B 5/1036; A61B 5/1038; A61B 5/6807
USPC .......................................... 600/587, 592, 595
See application file for complete search history.

(56) References Cited

U.S. PATENT DOCUMENTS

| | | | |
|---|---|---|---|
| 6,195,921 B1 | 3/2001 | Truong | |
| 6,836,744 B1 | 12/2004 | Asphahani et al. | |
| 8,261,611 B2 * | 9/2012 | Kim et al. | ........................ 73/172 |
| 2008/0108913 A1 * | 5/2008 | Lengsfeld et al. | ............ 600/595 |
| 2011/0146396 A1 | 6/2011 | Kim et al. | |

FOREIGN PATENT DOCUMENTS

| | | |
|---|---|---|
| KR | 1020070071308 A | 7/2007 |
| KR | 1020070100592 A | 10/2007 |
| KR | 1020080102466 A | 11/2008 |
| KR | 10-2011-0072328 A | 6/2011 |

* cited by examiner

*Primary Examiner* — Max Hindenburg
*Assistant Examiner* — Jonathan M Foreman (57) ABSTRACT

A method and apparatus for recognizing a gait pattern are provided. The method for recognizing a gate pattern includes: obtaining a walker's foot pressure distribution values through a pressure sensor array disposed at the bottom of a pair of shoes; calculating valid pressure points among the foot pressure distribution values; calculating a center of pressure (COP) movement trace by using the valid pressure points; and recognizing the walker's gait pattern by using the COP movement trace.

12 Claims, 6 Drawing Sheets

PRIOR ART

METHOD AND APPARATUS FOR ANALYZING GAIT PATTERN

CROSS-REFERENCE TO RELATED APPLICATIONS

This application claims the priority of Korean Patent Application No. 10-2010-0132340 filed on Dec. 22, 2010, in the Korean Intellectual Property Office, the disclosure of which is incorporated herein by reference.

BACKGROUND OF THE INVENTION

1. Field of the Invention

The present invention relates to a method and apparatus for analyzing a gait pattern and, more particularly, to a method and apparatus for analyzing a gait pattern to recognize a walker's (or a user's) gait pattern by using a movement trace of the center of pressure (COP) of the user's feet.

The present invention is derived from research conducted as a part of IT growth power industrial technology development work supported by the IT R&D program of MIC/IITA and the Knowledge Economics Department [Project Management No.: 2008-D-002-02, Project title: Promotion of Basis of Next-generation IT-based Technology Work].

2. Description of the Related Art

In a related art "Method for measuring exercise, balance, and walking ability and treatment system" (Korean Patent No. 10-0894895), a user's center of gravity (COG) and center of pressure (COP) are calculated by using a signal of a force sensing resistor (FSR) sensor in relation to the measurement of walking ability.

In the related art, a plurality of FSR sensors are used, and a maximum FSR output value is detected from the measured values and estimated as the COP. The algorithm for estimating the maximum FSR output value as the COP has a problem when it is applied to a general FSR array fabricated in the form of an insole of footwear, however.

The FSR sensor generates a high value when pressure is applied to an accurate point, in terms of its characteristics (here, it is assumed that the FSR sensor has a high output value with respect to a high pressure).

Figure 1:
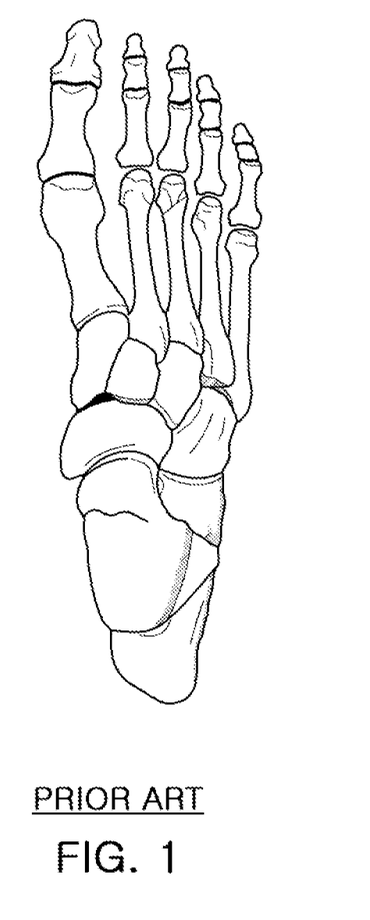
FIG. 1 is a view showing an example of a skeletal structure of a foot.

In this case, however, when the skeletal structure of foot, as shown in FIG. 1, is considered, an FSR sensor positioned in a portion to which a maximum pressure is not applied in actuality may output the highest value. For example, when the FSR sensor is accurately placed under the toe bone, although the strongest pressure is applied to a front portion of a first metatarsal, the FSR sensor positioned at the corresponding toe will output the highest value.

However, when the COP is calculated in consideration of the maximum pressure output value only, the skeletal structure of the foot and the characteristics of the pressure sensor cannot be properly reflected, degrading the accuracy of analysis of a gait pattern.

Also, in a case in which the COP is obtained by simply averaging the values of the entirety of provided pressure cells, a pressure value irrespective of the pressure generated according to wearing shoes or walking, or a pressure value irrespective of a foot pressure center shift, may be unnecessarily reflected in calculating the COP.

SUMMARY OF THE INVENTION

An aspect of the present invention provides a method and apparatus for analyzing a gait pattern capable of measuring a movement trace of a walker's center of pressure (COP) in consideration of the skeletal structure of a foot, the characteristics of a pressure sensor, and even a particularity in wearing shoes, and recognizing the walker's gait pattern, thus improving reliability and accuracy in an analysis operation.

Another aspect of the present invention provides a method and apparatus for analyzing a gait pattern capable of correcting a gait pattern based on gait pattern analysis results.

According to an aspect of the present invention, there is provided a method for analyzing a gait pattern, including: obtaining a walker's foot pressure distribution values through a pressure sensor array disposed on the bottom of a pair of shoes; calculating valid pressure points among the foot pressure distribution values; calculating a center of pressure (COP) movement trace by using the valid pressure points; and recognizing the walker's gait pattern by using the COP movement trace.

The calculating of the valid pressure points may include: excluding a pressure point having a reduced pressure value in comparison to a previous pressure value from the plurality of pressure points reflecting the foot pressure distribution values; determining whether it is an instant at which the ball of the foot comes into contact with the ground after the heel was in contact with the ground; and when it is an instant at which the ball of the foot comes into contact with the ground after the heel was in contact with the ground, excluding all of the pressure points of the heel area, among the plurality of pressure points reflecting the foot pressure distribution values, from the valid pressure points.

The calculating of the valid pressure points may further include: excluding a pressure point, having a pressure value smaller than a pre-set minimum pressure value among the plurality of pressure points reflecting the foot pressure distribution values, from the valid pressure points.

The method may further include: deleting a pressure point having a pressure value difference greater than a pre-set value from nearby pressure points, among the plurality of pressure points reflecting the foot pressure distribution values.

The calculating of the COP movement trace may include: calculating a COP by using the valid pressure points; and checking whether or not it is a period from a heal strike (HS) to a toe-off (TO) and adding the COP to the COP movement trace.

The method may further include: providing a guidance message corresponding to the walker's gait pattern to the walker.

The guidance message may be provided in the form of one or more of an image, text, a sound, and vibrations, or may be provided through a mobile device carried by the walker.

According to an aspect of the present invention, there is provided an apparatus for analyzing a gait pattern, including: a pressure sensor array disposed on the sole of a shoe to obtain a walker's foot pressure distribution values; a center of pressure (COP) movement trace calculation unit extracting valid pressure points from the foot pressure distribution values and calculating a COP movement trace by using the valid pressure points; and a gait pattern determining unit recognizing the walker's gait pattern by using the COP movement trace.

The COP movement trace calculation unit may exclude a pressure point having a reduced pressure value in comparison to a previous pressure value and a pressure point of a heel area obtained at the instant when the ball of the foot is brought into contact with the ground after the heel was in contact therewith, among a plurality of pressure points reflecting the foot pressure distribution values, from the valid pressure points.

The COP movement trace calculation unit may further have a function of additionally excluding a pressure point, having a pressure value smaller than a pre-set minimum pressure value among the plurality of pressure points, from the valid pressure points.

The apparatus may further include: a gait pattern correction unit generating a guidance message for correcting the walker's gait pattern when the walker's gait pattern is an abnormal gait pattern; and an alarm unit performing an alarm operation corresponding to the guidance message.

The alarm unit may output the guidance message through a monitor screen, a vibration element, and a speaker, or output the guidance message through a mobile device carried by the walker.

The guidance message may be provided in the form of one or more of an image, text, a sound, and vibrations.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Embodiments of the present invention will now be described in detail with reference to the accompanying drawings. The invention may, however, be embodied in many different forms and should not be construed as being limited to the embodiments set forth herein. Rather, these embodiments are provided so that this disclosure will be thorough and complete, and will fully convey the scope of the invention to those skilled in the art.

In the drawings, the shapes and dimensions may be exaggerated for clarity, and the same reference numerals will be used throughout to designate the same or like components.

When a certain portion "includes" a certain element, it may mean that it further includes another element, rather than excluding a different element, unless otherwise specified.

Figure 2:
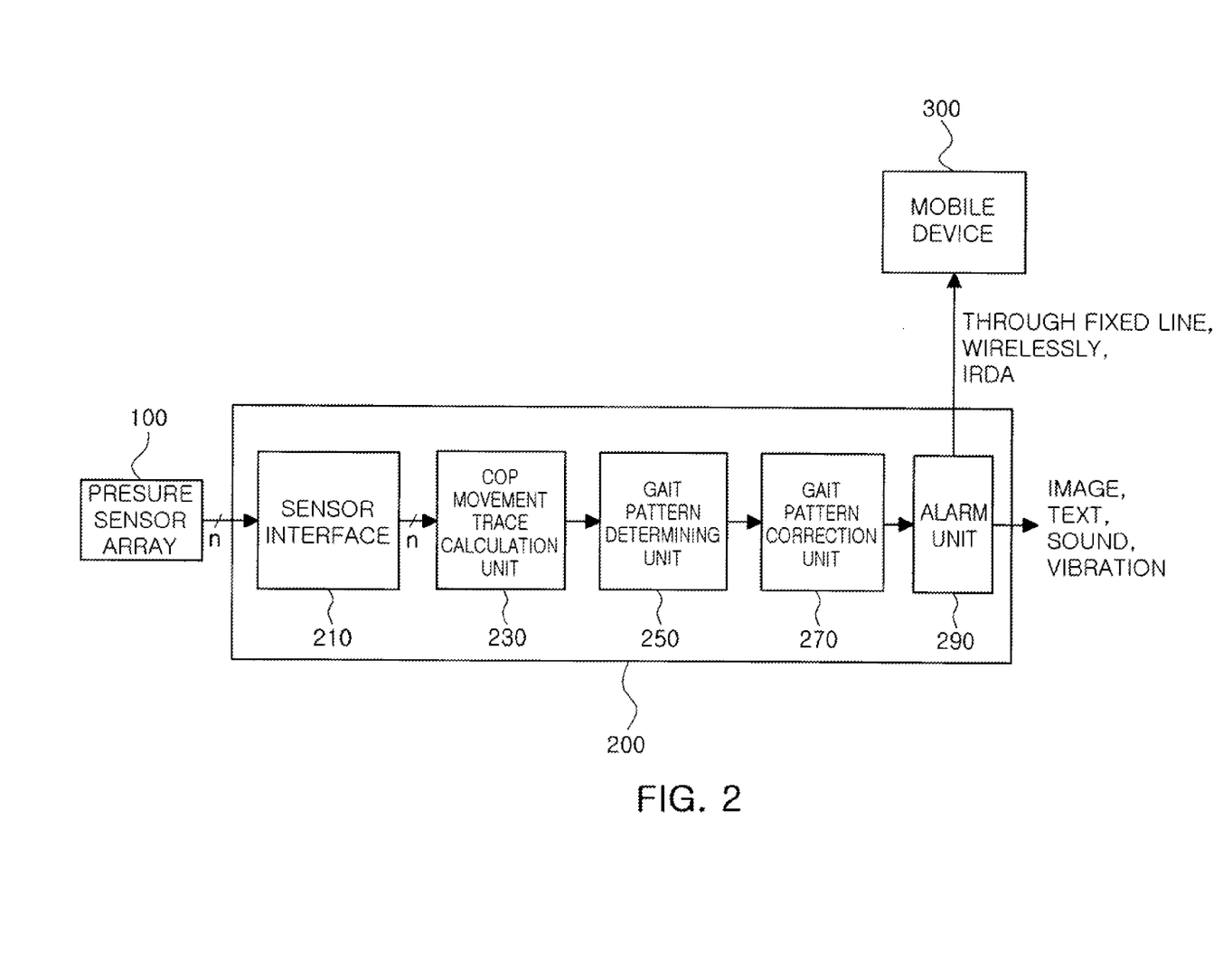
FIG. 2 is a schematic block diagram of an apparatus for analyzing a gait pattern according to an embodiment of the present invention.

FIG. 2 is a schematic block diagram of an apparatus for analyzing a gait pattern according to an embodiment of the present invention.

As shown in FIG. 2, the apparatus for analyzing a gait pattern according to an embodiment of the present invention may include a pressure sensor array 100, a sensor interface 210, a center of pressure (COP) movement trace calculation unit 230, a gait pattern determining unit 250, a gait pattern correction unit 270, an alarm unit 290, and the like.

Figure 4A:
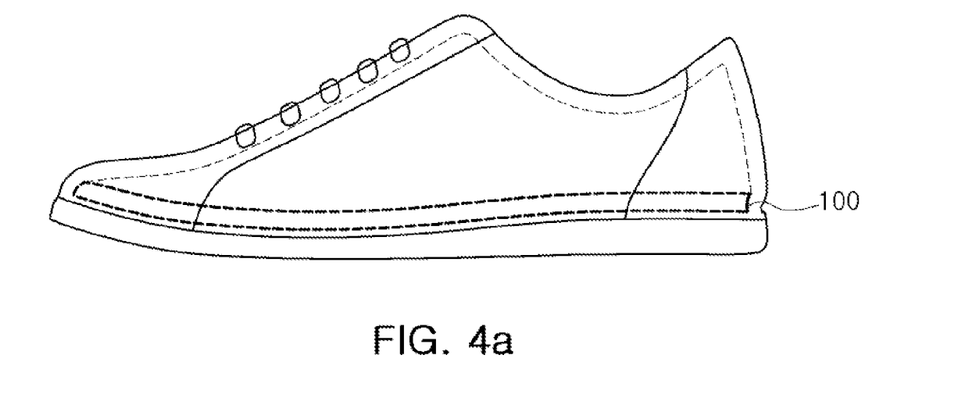
FIG. 4a and FIG. 4b are views showing the structure of the pressure sensor array according to an embodiment of the present invention.
Figure 4B:
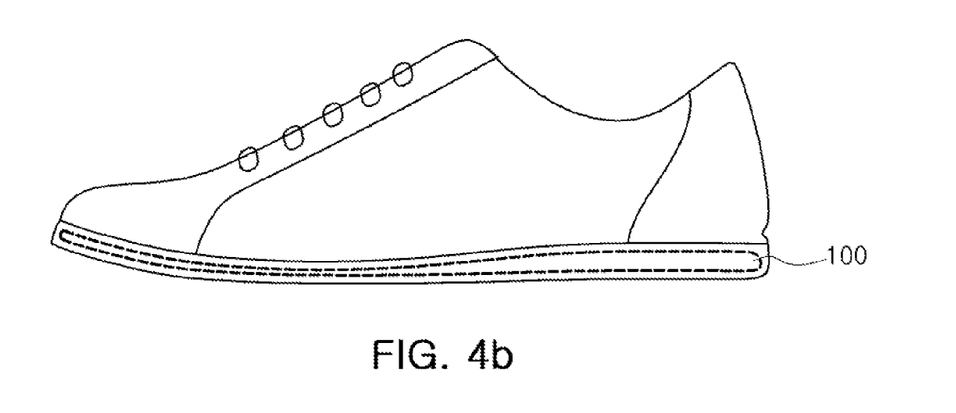

As shown in FIGS. 4a and 4b, the pressure sensor array 100 is disposed at the bottom of a pair of shoes (e.g., in the insole of a shoe, in the sole of a shoe, or the like) to measure foot pressure distribution values which are frequently changed according to a gait movement of a walker.

Figure 3:
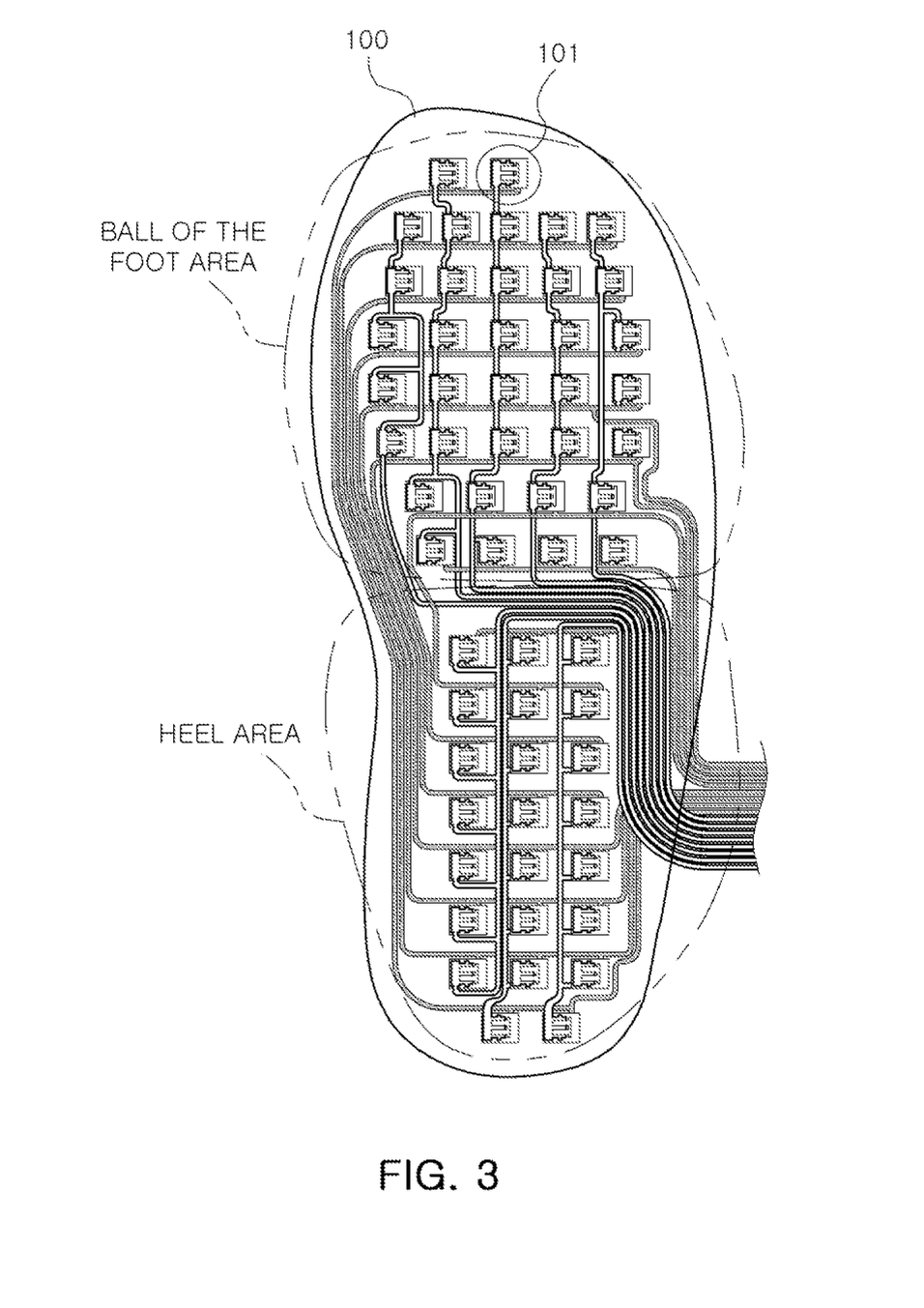
FIG. 3 is a view showing an example of a disposition of a pressure sensor array according to an embodiment of the present invention.

As shown in FIG. 3, the pressure sensor array 100 includes a plurality of force sensing resistor (FSR) sensors 101, and each of the FSR sensors 101 generates and outputs a signal having information regarding positions of pressure points and information regarding a pressure value. The arrangement form and the number of the FSR sensors 101 may vary in consideration of a gait pattern desired to be measured and measurement resolution.

The sensor interface 210 receives a plurality of signals output from the pressure sensor array 100, and converts the received signals into a data format which can be recognized by the COP movement trace calculation unit 230.

The COP movement trace calculation unit 230 extracts valid pressure points from the foot pressure distribution values measured by the pressure sensor array 100, and calculates a COP movement trace by using the valid pressure points.

The COP movement trace calculation operation of the COP movement trace calculation unit 230 is naturally performed during a period starting from a heal strike (HS) at which the walker's foot first comes into contact with the ground to a toe-off (TO) at which the walker's tiptoe is separated from the ground. Detection of the HO and TO follows a known technique and a detailed description thereof will be omitted.

The gait pattern determining unit 250 analyzes the COP movement trace calculated by the COP movement trace calculation unit 230 to determine a gait pattern of the walker.

When the gait pattern determined by the gait pattern determining unit 250 corresponds to an abnormal gait pattern such as an out-toed gait, in-toed gait, non-three counts gait, and the like, the gait pattern correction unit 270 generates a guidance message for correcting the walker's gait pattern.

The alarm unit 290 may include one or more of a monitor screen, a vibration element, and a speaker to directly provide a guidance message generated by the gait pattern correction unit 270 to the walker or may work integratedly with a mobile device 300 (e.g., a smartphone, or the like) carried by the walker to indirectly provide a guidance message to the walker through a display device (e.g., a monitor screen, a vibration element, a speaker, or the like) of the mobile device 300. Here, the guidance message may be provided in the form of one or more of an image, text, vibration, and sound to the walker.

Figure 5:
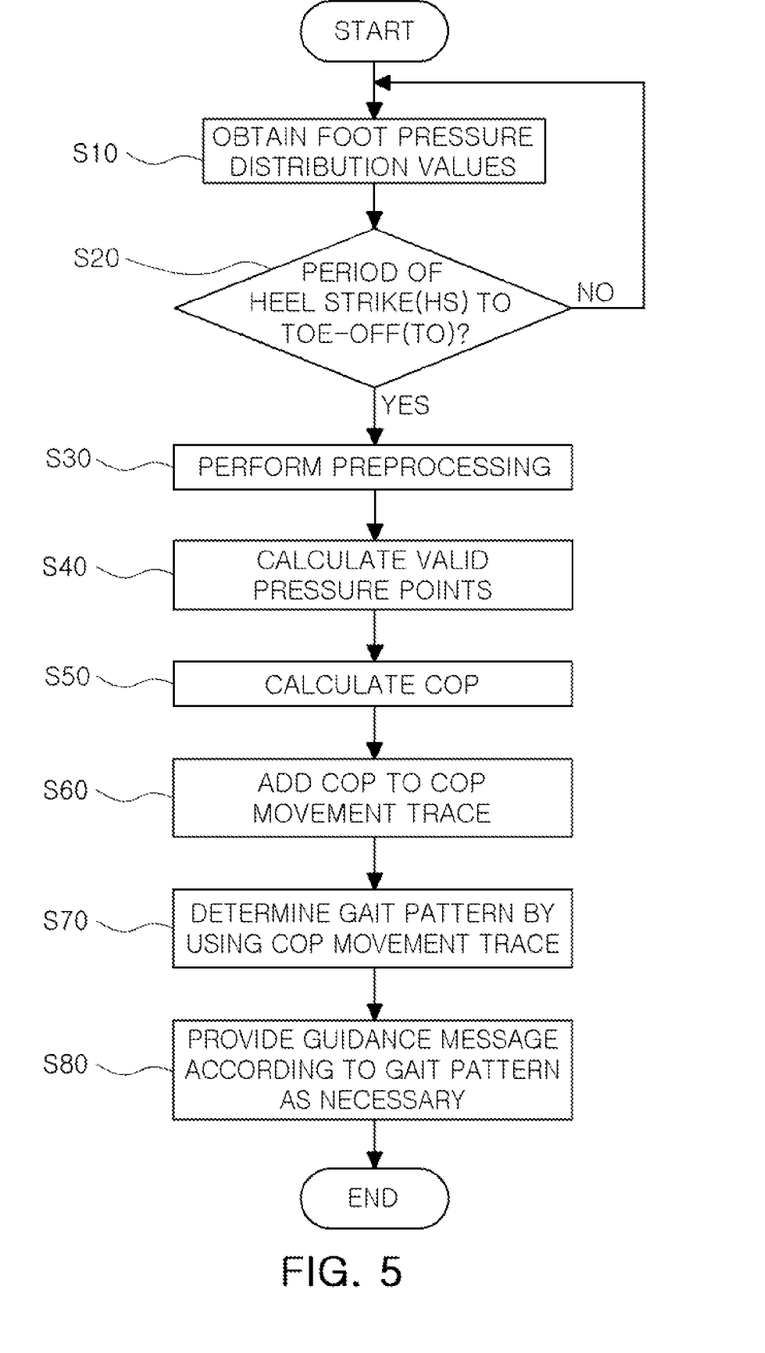
FIG. 5 is a flow chart illustrating a process of a method for analyzing a gait pattern according to an embodiment of the present invention.

FIG. 5 is a flow chart illustrating a process of a method for analyzing a gait pattern according to an embodiment of the present invention.

First, foot pressure distribution values of the walker are obtained through the pressure sensor array 100 (S10). When it is a period from the HS to the TO at which the walker's tiptoe is separated from the ground (S20), the walker's foot pressure distribution values are preprocessed to remove an island, a sensor error (S30).

At this time, an 'island' refers to an FSR sensor having a high signal value solely as compared with nearby FSR sensors which all have a low signal value. This problem arises when the shoe is instantly compressed, and this is performed only when the number of FSR sensors is sufficient. The reason is because when the number of the FSR sensors is not sufficient, an 'island' is highly likely to be output in actuality.

After valid pressure points are calculated from a plurality of signals obtained from the preprocessing (S40), and the COP is calculated by using the valid pressure points (S50). The valid pressure points refer to pressure points actually related to the COP of the walker which is shifted when the walker is walking.

The COP calculated in step S50 is added to a COP movement trace (S60), and when the period up to the TO at which the walker's tiptoe is separated from the ground expires (or has lapsed) (namely, when the entirety of the sole of the walker's foot is separated from the ground), the COP movement trace calculated up to now and a predefined normal gait pattern are compared to determine the walker's gait pattern (S70).

When the walker has an abnormal gait according to the determination results in step S70, the walker is informed of the current gait pattern to allow the walker to correct his gait posture (S80).

For example, when the walker has an out-toed gait, a guidance message stimulating one or more of the walker's sense of sight, sense of touch, and sense of hearing is provided to allow the walker to recognize that he is currently swaggering (i.e., he is walking with an out-toed gait) and guide him to walk normally.

Figure 6:
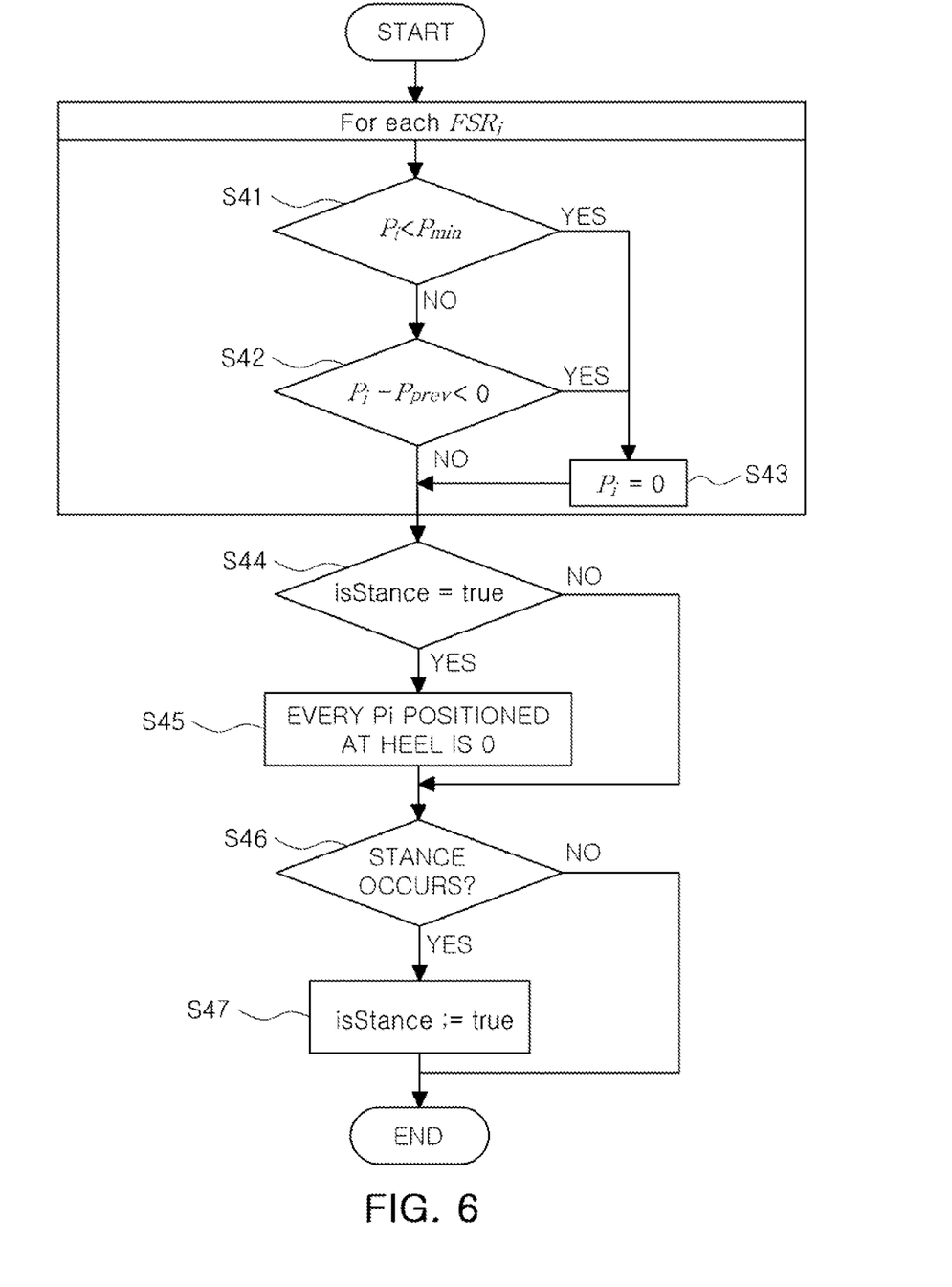
FIG. 6 is a flow chart illustrating a process of calculating a valid pressure point according to an embodiment of the present invention.

FIG. 6 is a flow chart illustrating a process of calculating a valid pressure point according to an embodiment of the present invention.

First, it is checked whether or not a pressure value Pi of a pressure point FSRi is smaller than a pre-set minimum pressure value Pmin (S41). Here, whether to perform step S41 may be determined by adjusting the value of the minimum pressure value Pmin.

When the pressure value Pi of a pressure point FSRi is equal to or greater than the minimum pressure value Pmin, the current pressure value Pi of the pressure point FSRi is compared with a previous pressure value Pprev to check whether or not the current pressure value Pi of the pressure point FSRi has been reduced compared with the previous pressure value (S42).

When the pressure value Pi of the pressure point FSRi is smaller than the minimum pressure value Pmin or when the pressure value Pi of the pressure point FSRi has been reduced according to the checking results in steps S41 and S42, Pi is set to 0 and the pressure point FSRi is indicated as a non-valid pressure point (S43).

When steps S41 to S43 are iteratively performed on all the pressure points, a state of isStance=true is checked (S44). When isStance=true, it is determined that it is an instant at which the ball of the foot currently comes into contact with the ground after the heel was in contact with the ground, and all of the pressure points corresponding to the heel area are removed from the valid pressure points (S45). In this case, when the ball of the foot comes into contact with the ground after the heel was in contact with the ground, an actual maximum pressure value must be actually generated from the ball of the foot area, and here, the removal is to prevent an operational error generated as the pressure sensor positioned at the heel of the foot area outputs an erroneous pressure value.

When step S45 is completed, the pressure of the non-valid pressure points have been all removed and only valid pressure points remain.

It is checked whether or not a Stance has occurred (S46). The Stance refers to a case in which front and rear portions of the foot are brought into contact with the ground after the foot is in contact with the ground in a gait stage. Namely, in this case, pressure points having a pressure value equal to or greater than a pre-set reference value simultaneously exist at both the front and rear portions of the foot.

When the Stance occurs, it is set such that isStance=true (S47). When isStance is initialized to be false, and when the toe is separated from the ground, it is initialized to be false again.

As set forth above, in the method and apparatus for analyzing a gait pattern according to embodiments of the invention, a movement trace is measured in consideration of the skeletal structure of a foot, the characteristics of a pressure sensor, and even particularity in wearing shoes, which are overlooked in the related art, based on which a gait pattern of the walker is recognized. As a result, reliability and accuracy of an analysis operation can be improved.

Also, because a guidance message for correcting the walker's gait pattern is provided in the form of one or more of an image, text, vibration, and a sound to the walker, the gait pattern correction effect can be maximized.

While the present invention has been shown and described in connection with the embodiments, it will be apparent to those skilled in the art that modifications and variations can be made without departing from the spirit and scope of the invention as defined by the appended claims.

What is claimed is:

1. A method for recognizing a gait pattern, the method comprising:
   obtaining a walker's foot pressure distribution values through a pressure sensor array disposed on a bottom of a pair of shoes;
   calculating valid pressure points among the foot pressure distribution values the valid pressure points excluding:
      a pressure point having a reduced pressure value in comparison to a previous pressure value among a plurality of pressure points reflecting the foot pressure distribution values; and
      all pressure points of a heel area during an instant at which a ball of the foot comes into contact with the ground after a heel of the foot is in contact with the ground;
   calculating a center of pressure (COP) movement trace by using the valid pressure points; and
   recognizing a walker's gait pattern by using the COP movement trace.

2. The method of claim 1, wherein the calculating of the valid pressure points further comprises excluding, from the valid pressure points, a pressure point having a pressure value smaller than a pre-set minimum pressure value among the plurality of pressure points reflecting the foot pressure distribution values.

3. The method of claim 1, further comprising:
   deleting a pressure point having a pressure value difference greater than a pre-set value from nearby pressure points, among the plurality of pressure points reflecting the foot pressure distribution values.

4. The method of claim 1, wherein the calculating of the COP movement trace comprises:
   calculating the COP by using the valid pressure points; and
   checking whether or not it is a period from a heel strike (HS) to a toe-off (TO) and adding the COP to the COP movement trace.

5. The method of claim 1, further comprising: providing a guidance message corresponding to the walker's gait pattern to the walker.

6. The method of claim 5, wherein the guidance message is provided in the form of one or more of an image, text, a sound, and vibrations.

7. The method of claim 5, wherein the guidance message is provided through a mobile device carried by the walker.

8. An apparatus for analyzing a gait pattern, the apparatus comprising:
   a pressure sensor array disposed on a sole of a shoe to obtain a walker's foot pressure distribution values;

a center of pressure (COP) movement trace calculation unit extracting valid pressure points from the foot pressure distribution values and calculating a COP movement trace by using the valid pressure points, the valid pressure points excluding a pressure point having a reduced pressure value in comparison to a previous pressure value and a pressure point of a heel area obtained at an instant when a ball of a foot is brought into contact with ground after a heel was in contact with the ground; and a gait pattern determining unit recognizing a walker's gait pattern by using the COP movement trace.

9. The apparatus of claim 8, wherein the COP movement trace calculation unit excludes from the valid pressure points a pressure point having a pressure value smaller than a pre-set minimum pressure value.

10. The apparatus of claim 8, further comprising:

a gait pattern correction unit generating a guidance message for correcting the walker's gait pattern when the walker's gait pattern is an abnormal gait pattern; and an alarm unit performing an alarming operation corresponding to the guidance message.

11. The apparatus of claim 10, wherein the alarm unit outputs the guidance message through a monitor screen, a vibration element, and a speaker, or outputs the guidance message through a mobile device carried by the walker.

12. The apparatus of claim 11, wherein the guidance message is provided in the form of one or more of an image, text, a sound, and vibrations.

* * * * *